United States Patent [19]

Suresh et al.

[11] Patent Number: 4,760,159

[45] Date of Patent: Jul. 26, 1988

[54] METHOD FOR AMMOXIDATION OF PARAFFINS AND CATALYST THEREFOR

[75] Inventors: Dev D. Suresh, Macedonia; David A. Orndoff, Windsor; James F. Brazdil, Mayfield Village; Linda C. Glaeser, Cleveland Heights; Maria S. Friedrich, Lyndhurst, all of Ohio

[73] Assignee: The Standard Oil Company, Cleveland, Ohio

[21] Appl. No.: 25,900

[22] Filed: Mar. 13, 1987

[51] Int. Cl.$^4$ .................................... C07C 120/14
[52] U.S. Cl. .................................. 558/319; 558/321; 558/324
[58] Field of Search .......................... 558/319

[56] References Cited

U.S. PATENT DOCUMENTS

| | | | |
|---|---|---|---|
| 3,221,507 | 5/1967 | Ginnasi et al. | 558/319 |
| 3,686,267 | 8/1972 | Taylor | 558/319 |
| 3,833,638 | 9/1974 | Knox et al. | 558/319 |
| 4,092,271 | 5/1978 | Sze | 558/319 X |

*Primary Examiner*—Joseph Paul Brust
*Attorney, Agent, or Firm*—C. S. Lynch; D. J. Untener; L. W. Evans

[57] ABSTRACT

Disclosed is a process for the vapor phase ammoxidation of a $C_3$ to $C_5$ paraffin to an $\alpha,\beta$-unsaturated nitrile having 3–5 C atoms, using a particulate bismuth-vanadium oxide catalyst containing at least one other specified element.

7 Claims, No Drawings

METHOD FOR AMMOXIDATION OF PARAFFINS AND CATALYST THEREFOR

This invention relates to an improved process for the catalytic ammoxidation of paraffins containing from 3 to 5 carbon atoms to $\alpha,\beta$-unsaturated nitriles, especially paraffins containing 3 to 4 carbon atoms. Most important is the ammoxidation of isobutane to methacrylonitrile and, especially, of propane to acrylonitrile.

Because of the price differential between propylene and propane an economic incentive exists for the development of a viable catalytic process for conversion of propane to acrylonitrile.

Earlier attempts in the prior art to develop an efficient process for the ammoxidation of propane to acrylonitrile produced either insufficient yields or processes that necessitated adding halogen promoters to the feed. The latter procedure would require not only reactors made of special corrosion resistant materials, but also the quantitative recovery of the promoter. The added costs thus eliminated the advantage of the propane/propylene price differential.

It is thus an object of the present invention to provide an improved process for the ammoxidation of paraffins to unsaturated nitriles.

Still another object is to provide an improved catalytic ammoxidation process for making unsaturated nitriles from lower paraffins without the use of halogen promoters.

Other objects, as well as aspects, features and advantages, of the present invention will become apparent from a study of the accompanying disclosure and the claims.

The foregoing and other objects of the present invention are achieved by the process of the present invention according to which there is provided a process for the ammoxidation of a $C_3$ to $C_5$ paraffin to an $\alpha,\beta$-unsaturated nitrile having 3–5 C atoms, which comprises contacting in a reaction zone said paraffin in the vapor phase in admixture with ammonia, molecular oxygen, and optionally an inert gaseous diluent, with a particulate catalyst having oxygen and the cation components indicated by the empirical formula, $$Bi_aV_bL_lM_mT_tO_x,$$

where

L is one or more of K, Cs, Rb and Tl;
M is one or more of Mo, W, Cr, Ge or Sb;
T is one or more of Ce, Zn, B, Nb and Ta, and
a = 1–25
b = 1–50
l = 0–1, usually 0–0.2
m = 0.1–20
t = 0–20
x is determined by the oxidation state of the other elements in the catalyst, $(a+b):(l+m+t) = 20:1-1:5$

a:b = 1:5–5:1, usually 1:3–3:1, said cation components being present in the catalyst in the proportions indicated by such formula.

The process of the invention is especially useful in the ammoxidation of propane or isobutane with $NH_3$ and $O_2$, to yield acrylonitrile or methacrylonitrile, respectively.

In the practice of the process of the invention the particulate catalyst can be used as such, but it usually contains an inorganic oxide support or diluent present as an integral part of each particle of catalyst. Such diluents are well known in the catalyst art and include silica, alumina, alundum, zirconia, titania, etc. We have found a silica-alumina support/diluent containing $SiO_2$:$Al_2O_3$ weight ratio in the range from 1:10 to 10:1, particularly from 4:6 to 6:4 to be especially useful. The support when present is not an oxide of an element of the foregoing empirical formula.

In the particulate catalyst compositions of the invention the empirical formula and does not, of course, connote any particular chemical compound, nor indicate whether the elements are present as a mixture of individual oxides or as a complex oxide or oxides, or what separate crystalline phases or solid solutions may be present. However, each particle of the catalyst contains the elements and proportions indicated by the foregoing formula. Similarly, the designation of certain oxides, such as "silica" or "alumina" or $SiO_2$ or $Al_2O_3$, as supports or diluents is merely in accordance with convention in the inorganic oxide catalyst art, and such designations refer to compounds often regarded as supports in the catalyst art. Such designations, however, do not mean that the element involved is actually present as a simple oxide. Indeed, such elements may at times by present as a complex oxide with one, more than one, or all of the elements in the foregoing empirical formula, which complex oxides form during the precipitation or agglomeration, drying and calcining process for preparing the catalyst composition.

In the ammoxidation of the present invention, the reaction is carried out in the gas phase by contacting a mixture containing the paraffin, ammonia and molecular oxygen, and inert diluent, if any, conveniently in a fixed bed of the catalyst, or a gravity flowing bed, a fluidized bed or a fast transport reactor mode.

In the present process the feed to the reaction zone contains a mole ratio of paraffin:$NH_3$ in the range from 0.2–16 (usually 0.4–5), and the mole ratio of paraffin:$O_2$ in the range from 0.1–10 (usually 0.2–5).

Moreover, the mole ratio of $O_2$ to $NH_3$ fed to the reaction zone is in the range from 1–10 (more often 1–5), and the mole ratio of inert gaseous diluent to paraffin is usually in the range from zero-20 (more often zero-12); of course, even higher molar ratios, say up to 50 diluent to 1 paraffin, can be used but are usually uneconomical.

In an especially useful aspect of the present invention an excess of paraffin is employed in relation to $NH_3$ and molecular oxygen. In such embodiment the usual ratio of paraffin:$NH_3$ is in the range from 2 to 16 (usually 2 or 3 to 7), and the mole ratio of paraffin:$O_2$ is in the range from 1 to 10 (usually 1.5 to 5), in the feed to the reaction zone. In this aspect of the invention, the usual ratio of $O_2$ to $NH_3$ is as before stated, but the ratio of inert gaseous diluent:paraffin is in the range from zero to 5, usually zero to 3.

In this aspect of the present process, i.e. when using excess paraffin, when applied to propane ammoxidation a small amount of propylene is produced in relation to the unreacted propane in the effluent. Thus the propane effluent containing propylene in the amount of up to 8 mole percent, but usually no more than 6 mole percent, of the amount of propane plus propylene can comprise the substrate feed to the present process.

And in general the $C_3$ to $C_5$ alkane feed to the reaction zone of the process of the present invention, whether or not an excess of paraffin is used, can contain one or more $C_3$ to $C_5$ olefins. The $C_3$ to $C_5$ olefin content of the feed to the present ammoxidation process can contain from zero to 8 mole percent of such olefin(s), based on the moles of $C_3$ to $C_5$ paraffin plus olefins fed, and this feed can be from any source. However, larger amounts of $C_3$ to $C_5$ olefins may be present in the substrate paraffin feed, but the usual proportions are as stated, and the usual olefin is that corresponding to the particular paraffin fed to the reaction zone of the present process.

Examples of inert diluents useful in the reaction zone are $N_2$, He, $CO_2$, $H_2O$ and Ar. When operating with an excess of the paraffin, such as propane, over the stoichiometric amount of $O_2$ and $NH_3$, the excess paraffin, such as propane, acts as a diluent and little or no added inert diluent is desirable in most cases.

The reaction temperature range can vary from 350° to 700°, but is usually 440° to 550° C. The latter temperature range is especially useful in the case of propane ammoxidation to acrylonitrile.

The average contact time can often be from 0.01 to 10 seconds, but is usually from 0.02 to 10 seconds, more usually from 0.05 to 5 seconds.

The pressure of the reaction usually ranges from 2 to 45 psia. Most often, pressure is somewhat above atmospheric, i.e. 1 to 8 psia above.

In any event, the pressure, temperature and contact times are not the essence of the invention and can be outside these ranges. The most advantageous combination of these conditions for a given desired result from a given feed can be determined by routine experimentation.

The following examples of the invention are exemplary and should not be taken as in any way limiting.

CATALYST EXAMPLE A

A catalyst having the composition, 50% $Bi_2V_3O_x$ + 50% $SiO_2$, was made as follows:

32.83 g of bismuth nitrate dissolved in dilute (10%) nitric acid was added to 11.9 g of ammonium metavanadate dissolved in hot water. 62.5 g of silica sol was added to this and the resultant slurry was evaporated to dryness over a hot plate. The dried material was heat treated at 290° C./3 hrs, 425° C./3 hrs and at 610° C./3 hrs.

CATALYST EXAMPLE B

A catalyst having the composition, 50% $BiVO_x$ + 25% $SiO_2$ + 25% $Al_2O_3$, was made as follows:

37.4 g of bismuth nitrate dissolved in dilute nitric acid (10%) was added to 9.0 g of ammonium metavanadate dissolved in hot water. 31.2 g of silica sol and 62.5 g alumina sol were added to this, and the resultant slurry was then worked up as in Example A.

CATALYST EXAMPLE C

This catalyst was the same as Catalyst B but heated in a stream of $NH_3$ at 460° C. for 15 minutes.

CATALYST EXAMPLE D

A catalyst with the composition 50% $BiV_{0.7}O_x$ + 25% $SiO_2$ + 25% $Al_2O_3$ was prepared in the manner described with respect to Example B.

CATALYST EXAMPLE 1

Bismuth nitrate dissolved in dilute nitric acid was mixed with a solution containing ammonium metavanadate and ammonium heptamolybdate dissolved in hot water. Silica sol and alumina sol were added to this and the slurry was evaporated to dryness over a hot plate. The dry material was heat treated at 290° C./3 hrs, 425° C./3 hrs and 610° C./3 hrs. The composition of the catalyst was 50% $BiV_{0.7}Mo_{0.5}O_x$ + 25% $SiO_2$ + 25% $Al_2O_3$.

CATALYST EXAMPLE 2

This catalyst was prepared as outlined in Example 1 but with the resultant composition being 50% $BiVMo_3O_x$ + 25% $SiO_2$ + 25% $Al_2O_3$.

CATALYST EXAMPLE 3

This catalyst was prepared as outlined in Example 1 except that $GeO_2$ was used instead of ammonium heptamolydate. The resultant composition was 50% $BiVGe_3O_x$ + 25% $SiO_2$ + 25% $Al_2O_3$. Following the 610° C. heat teatment, the catalyst was treated in a stream of ammonia at 460° C. for 15 minutes.

CATALYST EXAMPLE 4

Bismuth nitrate dissolved in dilute nitric acid was added to a mixture containing an aqueous solution containing ammonium metavanadate and antimony sol. An aqueous slurry of $Nb_2O_5$ was added to this, followed by the addition of silica sol and alumina sol. The resultant slurry was dried over a hot plate and the dry material was heat treated at 290° C./3 hrs, 425° C./3 hrs and 550° C./3 hrs. The composition of the catalyst was 50% $BiV_2SbNbO_x$ + 25% $SiO_2$ + 25% $Al_2O_3$.

CATALYST EXAMPLE 5

This catalyst with the composition 50% $BiV_2SbTaO_x$ + 25% $SiO_2$ + 25% $Al_2O_3$, was prepared as outlined in Example 4, except that $Ta_2O_5$ was used in place of $Nb_2O_5$ and the final heat treatment of the catalyst was at 610° C. instead of 550° C.

CATALYST EXAMPLE 6

This catalyst with the composition 50% $BiV_{0.7}Sb_{0.5}O_x$ + 25% $SiO_2$ + 25% $Al_2O_3$, was prepared as described in Example 1 except that $Sb_2O_5$ sol was used in place of ammonium heptamolybdate solution.

CATALYST EXAMPLE 7

A catalyst with the composition 50% $BiV_{0.7}Mo_{0.5}Zn_{0.5}O_x$+25% $SiO_2$+25% $Al_2O_3$ was prepared in the manner described in Example 1 except that zinc nitrate dissolved in water was added to the bismuth nitrate solution.

CATALYST EXAMPLE 8

This catalyst is the catalyst of Example 2 treated in a stream of $NH_3$ at 460° C. for 15 minutes.

CATALYST EXAMPLE 9

Bismuth nitrate dissolved in dilute nitric acid was mixed with a solution containing ammonium metavanadate and ammonium heptamolybdate dissolved in hot water. Silica sol and alumina sol were added to this and the slurry was evaporated to dryness over a hot plate. The dry material was heat treated at 290° C./3 hrs, 425° C./3 hrs and 610° C./3 hrs. The composition of the catalyst was 50% $BiV_{0.7}Mo_{0.5}O_x$+25% $SiO_2$+25% $Al_2O_3$.

CATALYST EXAMPLE 10

This catalyst is the catalyst of Example 9 subsequently treated in a stream of $NH_3$ at 460° C. for 15 minutes.

CATALYST EXAMPLE 11

This catalyst is the catalyst of Example 9 treated in a stream of $NH_3$ at 480° C. for 15 minutes, and then in a mixture of $1NH_3/4.5$ air (volume ratios) for 1 hour at 460° C.

CATALYST EXAMPLE 12

This catalyst with the composition 50% $Cs_{0.01}BiV_{0.7}Mo_{0.5}O_x$+25% $SiO_2$+25% $Al_2O_3$, was prepared as described in Example 1 except that cesium nitrate dissolved in water was mixed with bismuth nitrate solution. The catalyst after the 610° C. heat treatment was treated in a stream of $NH_3$ at 460° C. for 15 minutes and in a stream of $1NH_3/4.5$ air at 460° C. for 1 hour.

CATALYST EXAMPLE 13

This catalyst with the composition 50% $BiV_{0.7}MoO_x$+25% $SiO_2$+25% $Al_2O_3$ was prepared as described in Example 1, but was further treated in a stream of $NH_3$ at 460° C. for 15 minutes.

CATALYST EXAMPLE 14

This catalyst with the composition of 50% $BiV_{0.7}Mo_{0.2}O_x$+25% $SiO_2$+25% $Al_2O_3$ was prepared and treated in the same manner as the catalyst of Example 13.

CATALYST EXAMPLE 15

This catalyst is the catalyst of Example 1 treated in a stream of $NH_3$ for 15 minutes at 460° C.

CATALYST EXAMPLE 16

This catalyst with the composition of 50% $BiV_{1.4}Mo_{0.5}O_x$+25% $SiO_2$+25% $Al_2O_3$ was prepared and treated as described in Example 10.

CATALYST EXAMPLE 17

This catalyst with the composition of 50% $BiV_{0.7}Mo_{0.5}Cr_{0.5}O_x$+25% $SiO_2$+25% $Al_2O_3$ was prepared as in Example 1 except that chromium nitrate dissolved in water was added to the bismuth nitrate solution.

CATALYST EXAMPLE 18

A catalyst with the composition 50% $BiV_{0.7}Mo_{0.5}SbO_x$+25% $SiO_2$+25% $Al_2O_3$ was prepared as described in Example 1, except that $Sb_2O_5$ sol was added to the ammonium metavanadate and ammonium heptamolybdate solution.

CATALYST EXAMPLE 19

A catalyst with the composition 50% $BiV_{0.7}Mo_{0.5}NbO_x$+25% $SiO_2$+25% $Al_2O_3$ was prepared as described in Example 18 except that an aqueous slurry of $Nb_2O_5$ was used instead of $Sb_2O_5$ sol.

CATALYST EXAMPLE 20

This catalyst is the catalyst of Example 19 treated in a stream of $NH_3$ at 460° C. at 15 minutes.

CATALYST EXAMPLE 21

This catalyst with the composition 50% $BiV_{0.7}Mo_{0.5}Cr_{0.1}O_x$+25% $SiO_2$+25% $Al_2O_3$ was prepared in the manner described in Example 17.

CATALYST EXAMPLE 22

This catalyst with the composition 50% $BiV_{0.7}MoCr_{0.5}O_x$+25% $SiO_2$+25% $Al_2O_3$ was prepared in the manner described for Example 17.

CATALYST EXAMPLE 23

This catalyst with the composition 50% $BiV_{0.7}Mo_2Cr_{0.5}O_x$+25% $SiO_2$+25% $Al_2O_3$ was prepared in the manner described in Example 17.

CATALYST EXAMPLE 24

This catalyst with the composition 50% $BiV_{0.7}Mo_{0.5}Sb_{0.5}O_x$+25% $SiO_2$+25% $Al_2O_3$ was prepared in the manner described in Example 18, but was heat treated at 550° C. instead of 610° C. as the final temperature.

CATALYST EXAMPLE 25

This catalyst with the composition 50% $BiV_{0.7}MoSb_2O_x$+25% $SiO_2$+25% $Al_2O_3$ was prepared in the manner described in Example 18.

CATALYST EXAMPLE 26

This catalyst is the same as the catalyst of Example 25, except that the final heat treatment was at 550° C.

CATALYST EXAMPLE 27

This catalyst with the composition 50% $BiV_{0.7}Mo_{0.2}Sb_{0.3}O_x$+25% $SiO_2$+25% $Al_2O_3$ was prepared in the manner described for Example 18.

CATALYST EXAMPLE 28

This catalyst is the same as the catalyst of Example 24, except that the final calcination temperature was 550° C. instead of 610° C.

CATALYST EXAMPLE 29

This catalyst with the composition 50% $BiV_{0.7}W_{0.5}O_x$+25% $SiO_2$+25% $Al_2O_3$ was prepared as described in Example 1, except that ammonium metatungstate was used instead of ammonium heptamolybdate.

CATALYST EXAMPLE 30

This catalyst is the same as the catalyst of Example 29, but was subsequently treated in a stream of $NH_3$ at 460° C. for 15 minutes.

CATALYST EXAMPLE 31

This catalyst with the composition 50% $BiV_{0.7}W_{0.5}Cr_{0.5}O_x$+25% $SiO_2$+25% $Al_2O_3$ was prepared as described in Example 17, except that ammonium metatungstate was used instead of ammonium heptamolybdate.

CATALYST EXAMPLE 32

This catalyst with the composition 50% $BiV_{0.7}WCr_{0.5}O_x$+25% $SiO_2$+25% $Al_2O_3$ was prepared in the manner described in Example 31.

CATALYST EXAMPLE 33

This catalyst with the composition 50% $BiV_{0.7}W_2Cr_{0.5}O_x$+25% $SiO_2$+25% $Al_2O_3$ was prepared in the manner described in Example 31.

CATALYST EXAMPLE 34

This catalyst with the composition 50% $BiV_{0.7}W_{0.5}Cr_{0.5}Sb_{0.5}O_x$+25% $SiO_2$+25% $Al_2O_3$ was prepared in the manner described in Example 31 except the $Sb_2O_5$ sol was added to the V-W solution.

CATALYST EXAMPLE 35

This catalyst with the composition 50% $BiV_{0.7}W_{0.5}Cr_{0.5}Nb_{0.5}O_x$+25% $SiO_2$+25% $Al_2O_3$ was prepared in the manner described in Example 34 except that an aqueous slurry of $Nb_2O_5$ was used instead of the $Sb_2O_5$ sol.

CATALYST EXAMPLE 36

This catalyst with the composition 50% $BiV_{0.7}Mo_{0.5}W_{0.5}O_x$+25% $SiO_2$+25% $Al_2O_3$ was prepared in the manner described in Example 18 except that an aqueous solution of ammonium metatungstate was used instead of the $Sb_2O_5$ sol.

CATALYST EXAMPLE 37

This is the catalyst of Example 36 treated in a stream of $NH_3$ at 460° C. for 15 minutes and 1 $NH_3$/4.5 air at 460° C. for 1 hr.

CATALYST EXAMPLE 38

This catalyst with the composition 50% $BiV_{0.7}Mo_{0.5}Cr_{0.5}O_x$+50% $Al_2O_3$ was prepared as described in Example 17, except that Catapal $Al_2O_3$ was used instead of silica sol and alumina sol.

CATALYST EXAMPLE 39

This catalyst had the composition of Example 17 and was similarly made, except the source of $Al_2O_3$ was Catapal alumina instead of alumina sol.

CATALYST EXAMPLE 40

A catalyst with the composition 50% $BiV_{0.7}Mo_{0.5}Cr_{0.5}O_x$+40% $SiO_2$+10% $Al_2O_3$ was prepared in the manner described in Example 17, but the final heat treatment was at 550° C. instead of 610° C.

CATALYST EXAMPLE 41

A catalyst with the composition $BiV_{0.7}Mo_{0.5}Cr_{0.5}O_x$+45% $SiO_2$+5% $Al_2O_3$ was prepared in the manner in Example 40.

CATALYST EXAMPLE 42

A catalyst with the composition 75% $BiV_{0.7}Mo_{0.5}Cr_{0.5}O_x$+12.5% $SiO_2$+12.5% $Al_2O_3$ was prepared in the manner described in Example 40.

CATALYST EXAMPLE 43

This catalyst with the composition 50% $BiV_{0.7}W_{0.5}Cr_{0.5}B_{0.5}O_x$+25% $SiO_2$+25% $Al_2O_3$ was prepared in the manner described in Example 31 except that boric acid was added to the mixture containing V and W.

CATALYST EXAMPLE 44

A catalyst with the composition 50% $K_{0.01}BiV_{0.7}Mo_{0.5}O_x$+25% $SiO_2$+25% $Al_2O_3$ was prepared in the manner described in Example 1, except that a solution of potassium nitrate was added to the bismuth nitrate solution and the heat treated catalyst was treated in a stream of $NH_3$ at 460° C. for 15 minutes.

CATALYST EXAMPLE 45

A catalyst with the composition 50 weight percent $BiV_{0.7}Mo_{0.5}WO_x$+25 weight percent $SiO_2$+25 weight percent $Al_2O_3$ was made in the manner described for Example 36.

CATALYST EXAMPLE 46

A catalyst with the composition 50% $BiV_{0.7}Mo_{0.5}Cr_{0.5}O_x$+40% $SiO_2$+10% $Al_2O_3$ was made in the manner of Example 40 except that the final calcination temperature was 610° C. instead of 550° C.

In the following ammoxidation examples summarized in Table 1, the catalyst is in a tubular ⅜ inch I.D. stainless steel fixed bed reactor. The reactor is equipped with a preheat leg and is immersed in a temperature controlled molten salt bath. The feed is fed to the catalyst for one hour before collection of product, unless otherwise noted; the runs of each example last 30–60 minutes during which the product is collected for analysis.

4,760,159

TABLE 1

| Example No. | Catalyst Example No. | Catalyst[1] Composition | Mole Ratios C3/NH3/O2/N2/H2O | Temp, °C. | CT Secs[4] | Percent Propane Conversion | Propane: Mole % Conversion to | | | | | % Selectivity Based on Propane | | |
|---|---|---|---|---|---|---|---|---|---|---|---|---|---|---|
| | | | | | | | AN[2] | HCN | AN+HCN | C3=[3] | AN+C3= | AN | AN+HCN | AN+C3= |
| I | A | 50Bi2V3.50S[5] | 1/2/3/7/3 | 500 | 1.7 | 40.5 | 3.1 | 1.8 | 4.9 | 4.0 | 7.1 | 7.7 | 12.1 | 17.5 |
| II | B | 50BiV.25S + 25A[6] | " | " | 0.5 | 27.0 | 5.5 | 2.1 | 7.6 | 3.8 | 9.3 | 20.4 | 28.1 | 34.4 |
| III | B | " | " | " | 1.7 | 60.8 | 7.4 | 1.5 | 8.9 | 0.2 | 7.6 | 12.1 | 14.6 | 12.5 |
| IV[7] | C | " | " | " | 1.7 | 60.1 | 9.3 | 0.9 | 10.2 | 0.6 | 9.9 | 15.4 | 17.0 | 16.5 |
| V | D | 50BiV.7.25S + 25A | " | 470 | 0.5 | 16.2 | 2.1 | 0.4 | 2.5 | 3.8 | 5.9 | 12.9 | 15.4 | 36.4 |
| VI | B | 50BiV.25S + 25A | 5/1/2/0/1 | 500 | 0.3 | 12.6 | 1.3 | 0.6 | 1.9 | 4.1 | 5.4 | 10.5 | 15.1 | 42.8 |
| 1 | 2 | 50BiVMo.25S + 25A | 1/2/3/7/3 | " | 0.5 | 39.4 | 9.5 | 2.0 | 11.5 | 4.4 | 13.9 | 24.1 | 29.2 | 35.3 |
| 2(I)[7] | 8 | " | " | " | 0.5 | 37.2 | 14.4 | 3.0 | 17.4 | 4.5 | 18.9 | 38.8 | 46.8 | 50.8 |
| 3 | 1 | 50BiV.7Mo.5.25S + 25A | " | " | 0.5 | 30.1 | 15.0 | 0.4 | 15.4 | 3.5 | 18.5 | 50.0 | 51.2 | 61.5 |
| 4 | 9 | " | " | " | 0.5 | 43.3 | 19.9 | 1.5 | 21.4 | 1.3 | 22.7 | 46.0 | 49.4 | 52.4 |
| 5(I) | 15 | " | 1/2/3/7/3 | " | 1.0 | 53.0 | 26.1 | 2.9 | 29.0 | 0.9 | 27.0 | 49.1 | 54.7 | 50.9 |
| 6(8) | 10 | " | " | " | 1.7 | 37.0 | 20.8 | 2.6 | 23.4 | 2.6 | 23.4 | 56.1 | 63.2 | 63.2 |
| 7(I) | 11 | " | " | " | 1.0 | 45.5 | 23.3 | 2.2 | 25.5 | 1.9 | 25.2 | 51.2 | 56.0 | 55.4 |
| 8(I) | 14 | 50BiV.7Mo2.25S + 25A | " | " | 0.9 | 26.9 | 12.9 | 1.9 | 14.8 | 2.9 | 15.8 | 47.9 | 55.0 | 58.7 |
| 9(I) | 16 | 50BiV.7Mo.4.25S + 25A | " | " | 1.0 | 53.7 | 17.6 | 1.8 | 19.4 | 2.3 | 19.9 | 32.4 | 36.1 | 37.1 |
| 10(I) | 13 | 50BiV.7Mo.5.25S + 25A | " | " | 1.0 | 50.1 | 25.0 | 2.5 | 27.5 | 2.8 | 27.8 | 49.8 | 54.9 | 55.5 |
| 11(9) | 13 | " | 5/1/2/0/1 | 470 | 0.5 | 12.8 | 6.6 | 0.3 | 6.9 | 1.9 | 8.5 | 51.5 | 53.9 | 66.4 |
| 12 | 1 | " | " | 450 | 0.4 | 10.2 | 4.8 | 0.9 | 5.7 | 2.3 | 7.1 | 47.3 | 55.9 | 69.6 |
| 13 | 1 | " | " | 470 | 0.4 | 13.2 | 6.8 | 0.8 | 7.6 | 2.4 | 9.2 | 51.3 | 57.6 | 69.7 |
| 14 | 1 | " | " | " | 0.6 | 13.3 | 6.7 | 0.4 | 7.1 | 2.4 | 9.1 | 50.5 | 53.4 | 68.4 |
| 15(10) | 1 | " | 1/2/3/7/3 | " | 0.5 | 13.4 | 6.6 | 0.4 | 7.0 | 2.7 | 9.3 | 49.6 | 52.2 | 69.4 |
| 16 | 44 | 50K.01BiV.7Mo.5.25S + 25A | " | " | 0.4 | 10.9 | 5.7 | 0.4 | 6.1 | 1.7 | 7.4 | 52.4 | 56.0 | 67.9 |
| 17 | 17 | BiV.7Mo.5Cr.5.25S + 25A | " | " | 0.5 | 13.0 | 5.4 | 0.3 | 5.7 | 2.9 | 8.3 | 41.7 | 43.8 | 63.8 |
| 18 | 46 | 50BiV.7Mo.5Cr.5.40S + 10A | " | " | 1.0 | 13.7 | 6.6 | 0.6 | 7.2 | 2.4 | 9.0 | 48.6 | 52.6 | 65.7 |
| 19(I)(11) | 3 | 50BiVGe3.25S + 25A | " | " | 1.7 | 54.3 | 18.2 | 6.1 | 24.3 | 0.6 | 18.8 | 33.5 | 44.8 | 34.6 |
| 20 | 4 | 50BiV2SbNb.25S + 25A | " | 500 | 1.8 | 67.6 | 13.1 | 2.9 | 16.0 | 5.4 | 18.5 | 19.4 | 23.7 | 27.4 |
| 21 | 5 | 50BiV2SbTa.25S + 25A | " | 480 | 1.8 | 58.4 | 10.4 | 1.0 | 11.4 | 5.6 | 16.0 | 17.8 | 19.5 | 27.4 |
| 22 | 6 | 50BiV.7Sb.5.25S + 25A | " | " | 0.5 | 17.3 | 5.5 | 1.1 | 6.6 | 0.3 | 5.8 | 31.8 | 38.2 | 33.5 |
| 23 | 7 | 50BiV.7Mo.5Zn.5.25S + 25A | 1/2/3/6.7/3.3 | 500 | 1.0 | 31.2 | 17.2 | 1.4 | 18.6 | 1.9 | 19.1 | 54.9 | 59.6 | 61.2 |
| 24(I) | 12 | 50Cs.01BiV.7Mo.5.25S + 25A | 1/2/3/7/3 | " | 0.9 | 38.5 | 19.3 | 2.0 | 21.3 | 2.5 | 21.8 | 50.0 | 55.3 | 56.6 |
| 25(I) | 12 | " | " | " | 1.9 | 55.0 | 23.9 | 2.7 | 26.6 | 1.7 | 25.6 | 43.5 | 48.4 | 46.5 |
| 26(I) | 12 | " | " | 480 | 1.9 | 41.2 | 18.9 | 3.1 | 22.0 | 2.1 | 21.0 | 45.8 | 53.4 | 51.0 |
| 27(I) | 12 | " | " | 500 | 3.6 | 71.1 | 17.5 | 0.3 | 17.8 | 1.6 | 19.1 | 24.6 | 25.0 | 26.9 |
| 28(I) | 12 | " | 1/2/3/7/7 | " | 1.5 | 43.0 | 23.6 | 2.1 | 25.7 | 2.2 | 25.8 | 55.0 | 59.8 | 60.0 |
| 29 | 12 | 50Cs.01BiV.7Mo.5.25S + 25A | 1/2/3/12/0 | " | 0.1 | 39.1 | 17.8 | 1.7 | 19.5 | 2.3 | 20.1 | 44.9 | 49.4 | 50.9 |
| 30(I) | 12 | " | 1/2/4/16/0 | 500 | 1.1 | 38.1 | 14.6 | 0.9 | 15.5 | 2.5 | 17.1 | 38.2 | 40.7 | 44.9 |
| 31 | 29 | 50BiV.7W.5.25S + 25A | 1/2/3/7/3 | " | 0.5 | 37.1 | 17.1 | 3.7 | 20.8 | 0.5 | 17.6 | 46.0 | 56.1 | 47.4 |
| 32(I) | 30 | " | " | " | 0.9 | 62.0 | 24.9 | 4.1 | 29.0 | 1.6 | 26.5 | 40.1 | 46.8 | 42.7 |
| 33 | 31 | 50BiV.7W.5Cr.5.25S + 25A | " | " | 0.9 | 76.5 | 20.9 | 3.7 | 24.6 | 1.4 | 22.3 | 27.4 | 32.2 | 29.2 |
| 34 | 32 | " | " | " | 1.0 | 69.3 | 20.0 | 3.0 | 23.0 | 0.6 | 20.6 | 28.8 | 33.2 | 29.7 |
| 35 | 43 | 50BiV.7W.5Cr.5B.5.25S + 25A | " | " | 1.0 | 65.3 | 26.1 | 4.3 | 30.4 | 1.5 | 26.6 | 40.0 | 46.6 | 40.7 |
| 36 | 33 | 50BiV.7W.5Cr.5Sb.5.5 + 25A | " | " | 1.0 | 69.2 | 15.0 | 1.8 | 16.8 | 1.0 | 16.0 | 21.2 | 24.3 | 23.1 |
| 37 | 34 | 50BiV.7W.5Cr.5Nb.5 + 25A | " | " | 1.0 | 71.8 | 22.4 | 4.7 | 27.1 | 1.8 | 24.2 | 31.3 | 37.7 | 33.7 |
| 38 | 35 | 50BiV.7Mo.5Cr.5.25S + 25A | " | " | 1.0 | 66.8 | 21.3 | 6.2 | 27.5 | 1.3 | 22.7 | 31.9 | 41.2 | 34.0 |
| 39 | 17 | " | " | " | 0.9 | 57.8 | 26.2 | 2.0 | 28.2 | 1.4 | 27.6 | 45.3 | 48.8 | 47.8 |
| 40 | 21 | 50BiV.7MoCr1.25S + 25A | " | " | 0.5 | 52.6 | 24.2 | 2.9 | 27.1 | 1.4 | 25.5 | 46.0 | 51.5 | 48.5 |
| 41 | 22 | 50BiV.7Mo.5Cr.5.25S + 25A | " | " | 1.0 | 50.4 | 20.0 | 0.5 | 20.5 | 1.3 | 21.7 | 39.7 | 40.7 | 43.1 |
| 42 | 23 | 50BiV.7MoCr.5.25S + 25A | " | " | 1.0 | 46.7 | 17.6 | 1.3 | 18.9 | 1.7 | 19.6 | 37.6 | 40.5 | 42.0 |
| 43 | 38 | 50BiV.7Mo.5Cr.5.50Al2O3 | " | " | 0.5 | 75.7 | 20.5 | 2.0 | 22.5 | 2.0 | 21.9 | 27.1 | 29.7 | 28.9 |
| 44 | 39 | 50BiV.7Mo.5Cr.5.25S + 25A | 1/2/3/7/3 | 500 | 0.9 | 69.7 | 23.3 | 2.6 | 25.9 | 1.2 | 24.5 | 33.4 | 37.2 | 35.2 |

TABLE 1-continued

| Example No. | Catalyst Example No. | Catalyst(1) Composition | Mole Ratios C3/NH3/O2/N2/H2O | Temp, °C. | CT Secs(4) | Percent Propane Conversion | Propane: Mole % Conversion to | | | | | % Selectivity Based on Propane | | |
|---|---|---|---|---|---|---|---|---|---|---|---|---|---|---|
| | | | | | | | AN(2) | HCN | AN + HCN | C3=(3) | AN + C3= | AN | AN + HCN | AN + C3= |
| 45 | 40 | 50BiV.7Mo.5Cr.5,40S + 10A | " | " | 0.9 | 72.4 | 27.2 | 5.4 | 32.6 | 2.2 | 29.4 | 37.6 | 45.0 | 40.6 |
| 46 | 40 | " | " | 475 | 1.9 | 74.2 | 20.1 | 4.5 | 24.6 | 1.6 | 21.7 | 27.1 | 33.2 | 29.2 |
| 47 | 41 | 50BiV.7Mo.5Cr.5,45S + 5A | " | 500 | 0.9 | 37.5 | 15.1 | 3.3 | 18.4 | 1.3 | 17.4 | 40.4 | 49.1 | 46.4 |
| 48 | 42 | 75BiV.7Mo.5Cr.5,12.5S + 12.5A | " | " | 0.9 | 64.3 | 14.6 | 2.4 | 17.0 | 1.5 | 16.1 | 22.8 | 26.4 | 25.0 |
| 50 | 19 | 50BiV.7Mo.5Nb.25S + 25A | " | " | 0.9 | 44.0 | 20.8 | 3.2 | 24.0 | 3.3 | 24.1 | 47.3 | 54.5 | 54.8 |
| 51(1) | 20 | " | " | " | 1.0 | 50.5 | 21.6 | 3.8 | 25.4 | 2.9 | 24.5 | 42.7 | 50.3 | 48.5 |
| 52 | 18 | 50BiV.7Mo.5Sb.25S + 25A | " | " | 1.0 | 49.6 | 22.4 | 3.2 | 25.6 | 4.6 | 27.0 | 45.1 | 51.6 | 54.4 |
| 53(1) | 24 | 50BiV.7Mo.5Sb.5,25S + 25A | " | " | 1.0 | 42.4 | 22.1 | 2.6 | 24.7 | 3.6 | 25.7 | 52.0 | 58.3 | 60.6 |
| 54 | 25 | 50Bi.5V.5MoSb2,25S + 25A | " | " | 1.0 | 45.0 | 15.8 | 4.8 | 20.6 | 4.8 | 20.6 | 35.0 | 45.8 | 45.8 |
| 55(1) | 26 | " | " | " | 1.0 | 58.8 | 18.6 | 5.0 | 23.6 | 5.4 | 24.0 | 31.7 | 40.1 | 40.8 |
| 56 | 27 | 50BiV.7Mo.2Sb.3,25S + 25A | " | " | 0.9 | 39.2 | 17.8 | 3.8 | 21.1 | 3.5 | 21.3 | 45.4 | 53.8 | 54.3 |
| 57 | 28 | 50BiV.7Mo.5Sb.5,25S + 25A | " | " | 1.0 | 38.8 | 21.2 | 3.3 | 25.5 | 5.8 | 27.0 | 54.6 | 65.7 | 69.6 |
| 58 | 28 | " | " | " | 3.0 | 60.8 | 29.6 | 3.3 | 32.9 | 3.2 | 32.8 | 48.6 | 54.1 | 53.9 |
| 59 | 36 | 50BiV.7Mo.5N.5,25S + 25A | 1/2/3/7/3 | 500 | 0.9 | 48.3 | 16.8 | 0.8 | 17.6 | 1.6 | 18.4 | 34.7 | | |
| 60(1) | 37 | " | " | " | 0.9 | 53.1 | 18.8 | 2.2 | 21.0 | 1.7 | 20.5 | 35.4 | | |
| 61 | 45 | 50BiV.7Mo.5W.25S + 25A | " | " | 1.0 | 53.4 | 19.8 | 1.4 | 21.2 | 1.3 | 21.1 | 37.1 | | |

(1)See Catalyst Examples for details of heat treatments, reducing pretreatment, etc.; $O_x$ is omitted from composition.
(2)AN is Acrylonitrile
(3)C3= is Propylene
(4)Contact Time, Seconds
(5)S is $SiO_2$
(6)A is $Al_2O_3$
(7)The feed was fed to the reactor for 16 hours before collecting products for analysis.
(8)The feed was fed to the reactor for 25.5 hours before collecting product for analysis.
(9)Catalyst not pre-reduced with $NH_3$
(10)The feed was fed to the reactor for 24 hours before collecting product for analysis
(11)The feed was fed to the reactor for 24 hours before collecting product for analysis
(12)The feed was fed to the reactor for 20 hours before collecting product for analysis.

As will be evident to those skilled in the art, various modifications of this invention can be made or followed in the light of the foregoing disclosure and discussion without departing from the spirit and scope of the disclosure or from the scope of the claims.

We claim:

1. A process for the ammoxidation of a $C_3$ to $C_5$ paraffin to an $\alpha,\beta$-unsaturated nitrile having 3–5 C atoms, which comprises contacting in a reaction zone said paraffin in the vapor phase in admixture with ammonia, molecular oxygen, and optionally an inert gaseous diluent, with a particulate catalyst having oxygen and the cation components indicated by the empirical formula, $$Bi_a V_b L_l M_m T_t O_x,$$

where

L is one or more of K, Cs, Rb and Tl;
M is one or more of Mo, W, Cr, Ge or Sb;
T is one or more of Ce, Zn, B, Nb, and Ta; and
a = 1–25
b = 1–50
l = 0–1
m = 0.1–20
t = 0–20
x is determined by the oxidation state of the other elements in the catalyst, $$(a+b):(l+m+t) = 20:1-1:5$$

$$a:b = 1:5-5:1$$

said cation components being present in the catalyst in the proportions indicated by such formula.

2. A process of claim 1 wherein said paraffin comprises propane.

3. A process of claim 1 wherein said catalyst contains a silica-alumina support/diluent having a weight ratio of $SiO_2:Al_2O_3$ in the range from 1:10 to 10:1.

4. A process for the ammoxidation of a $C_3$ to $C_5$ paraffin to an $\alpha,\beta$-unsaturated nitrile having 3–5 C atoms, which comprises contacting in a reaction zone said paraffin in the vapor phase in admixture with ammonia, molecular oxygen, and optionally an inert gaseous diluent, the feed to the reaction zone containing a mole ratio of paraffin:$NH_3$ in the range from 2 to 16 and a mole ratio of paraffin to $O_2$ in the range from 1 to 10, with a particulate catalyst having oxygen and the cation components indicated by the empirical formula, $$Bi_a V_b L_l M_m T_t O_x,$$

where

L is one or more of K, Cs, Rb and Tl;
M is one or more of Mo, W, Cr, Ge or Sb;
T is one or more of Ce, Zn, B, Nb, and Ta; and
a = 1–25
b = 1–50
l = 0–1
m = 0.1–20
t = 0–20
x is determined by the oxidation state of the other elements in the catalyst, $$(a+b):(l+m+t) = 20:1-1:5$$

$$a:b = 1:5-5:1$$

said cation components being present in the catalyst in the proportions indicated by such formula.

5. A process of claim 4 wherein said paraffin comprises propane.

6. A process of claim 4 wherein said catalyst contains a silica-alumina support/diluent having a weight ratio of $SiO_2:Al_2O_3$ in the range from 1:10 to 10:1.

7. A process of claim 4 wherein the paraffin contains zero to 8 mole percent $C_3$ to $C_5$ olefins, based on the total moles of $C_3$ to $C_5$ paraffins plus $C_3$ to $C_5$ olefins fed to the reaction zone.

* * * * *